Nov. 10, 1970 E. S. BOERNER Plant Pat. 2,998
ROSE PLANT
Filed Nov. 25, 1968
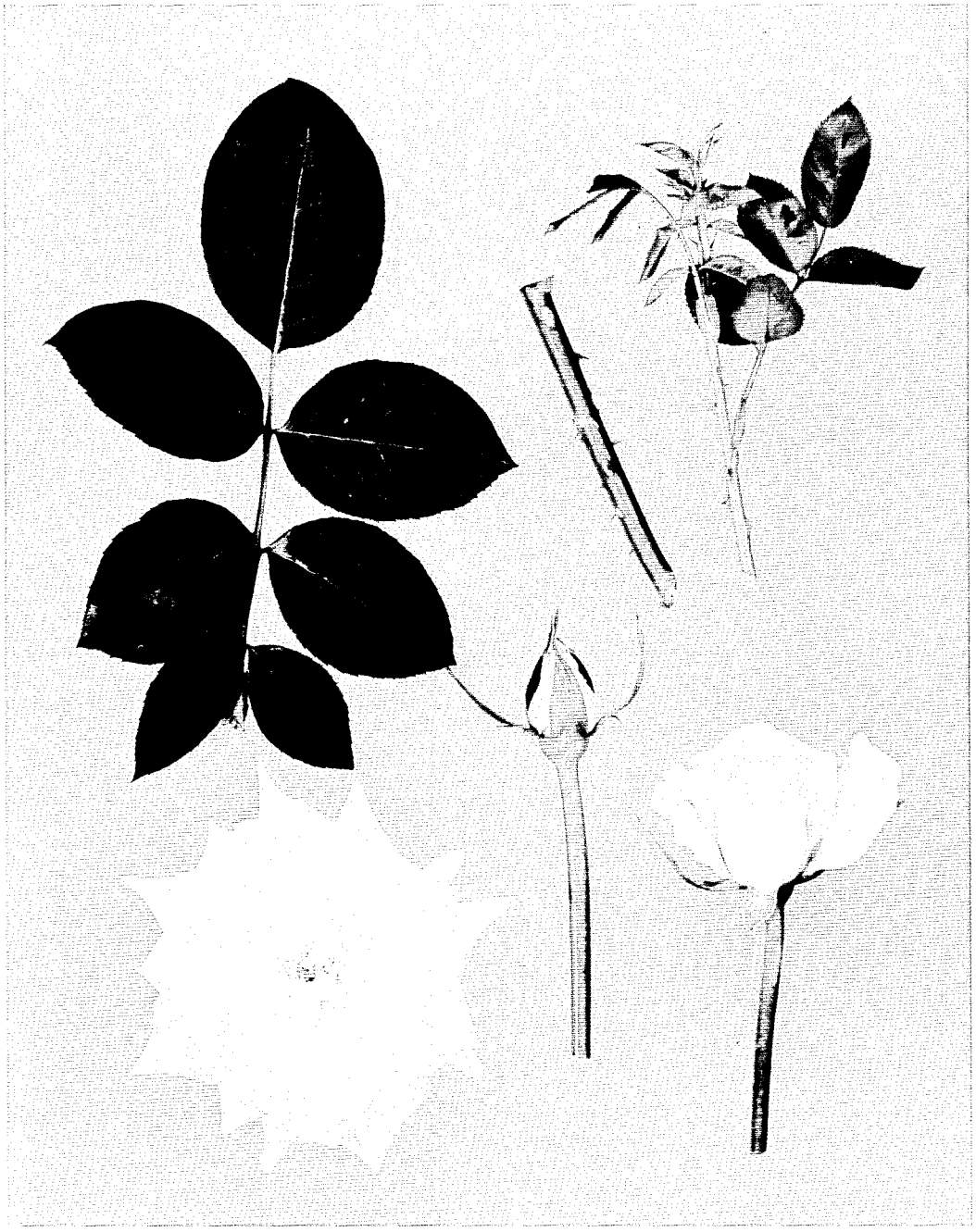
Inventor.
E. S. Boerner, Deceased
By: Lincoln Rochester Trust Company
By: Edward L. Jenner, Trust Officer
and Roger L. Boerner
Executors.
By: Robb & Robb, Attorneys.

United States Patent Office

Plant Pat. 2,998
Patented Nov. 10, 1970

2,998
ROSE PLANT

Eugene S. Boerner, deceased, late of Benton, N.Y., by Lincoln Rochester Trust Company, Geneva, N.Y., and Roger L. Boerner, executors, Milwaukee, Wis., assignors to Jackson & Perkins Company, Newark, N.Y., a corporation of New York Filed Nov. 25, 1968, Ser. No. 779,287
Int. Cl. A01h 5/00
U.S. Cl. Plt.—14 1 Claim The present invention relates to a new and distinct variety of rose plant of the hybrid tea class, which was originated by the late Eugene S. Boerner, deceased, by crossing an unnamed and unpatented pink-flowered seedling derived from crossing the rose variety known as "Revelry" (Plant Pat. No. 1,850) X the rose variety known as "Pink Masterpiece" (Plant Pat. No. 2,294) with an unnamed and unpatented pink-flowered seedling of unidentified parentage but designated at #60–2351 in applicant's breeding records.

The primary objective of this breeding was to produce a new and improved rose variety of the hybrid tea class which bears large, well-formed flowers on a vigorous and disease resistant plant. This objective was fully achieved, along with other desirable features, and the new variety embodies a unique combination of characteristics of which the following are outstanding therein and which distinguish the new variety from its parents, as well as from all other rose varieties:

(1) A large plant size;

(2) Exceptionally large and leathery leaves which are very resistant to mildew and blackspot;

(3) Continuous flower production throughout the year when grown in the greenhouse;

(4) A classical, spiral opening flower form, with the flowers being borne on long and unusually thick stems;

(5) A distinctive and attractive white flower color, with the flowers being larger than those of any other white-flowered variety grown in the same environment; and (6) Very long keeping qualities of the flowers.

Asexual reproduction of the new variety by budding, as performed at Livermore, Calif., shows that the aforementioned characteristics and distinctions come true to form and are established and transmitted through succeeding propagations.

The accompany drawing shows typical specimens of the vegetative growth and flowers of the new variety in different stages of development and as depicted in color as nearly true as it is reasonably possible to make the same in a color illustration of this character.

The following is a detailed description of the new rose variety, with color terminology in accordance with Ridgway's Color Standards and Nomenclature, except where general color terms of orginary dictionary significance are obvious:

Parentage: Seedling.
- *Seed parent.*—An unnamed pink-flowered seedling of "Revelery" X "White Masterpiece."
- *Pollen parent.*—An unnamed pink-flowered seedling of unidentified parentage.

Classification:
- *Botanic.*—Rosa.
- *Commercial.*—Hybrid tea.

Propagation: Holds its distinguishing characteristics through succeeding propagations by budding.

FLOWER (Observations made from specimens grown in a greenhouse at Newark, N.Y., in the afternoon during late October.)

Blooming habit: Continuous throughout the year when grown in the greenhouse.

Bud:
- *Size.*—Large.
- *Form.*—Ovoid; pointed tip.
- *Color.*—When sepals first divide: Pale Viridine Yellow, Plate 5, 29–f. When petals begin to unfurl: Between Seafoam Yellow, Plate 31, 25″–f and white; outer guard petals overcast with shadings of Kildare Green, Plate 31, 29″–b. When half-blown: Both sides of petals between Seafoam Yellow, Plate 31, 25″–f and white, with base of petals on inside Light Chalcedony Yellow, Plate 17, 25′–d.
- *Sepals.*—Edges nearly smooth with fine hairs; curl back when flower is fully open. Color: Outside surface—Light Bice Green, Plate 17, 29′–i. Inside surface—Light Bice Green, Plate 17, 29′.
- *Receptacle.*—Shape: Broad funnel. Surface: Smooth. Color: Light Bice Green, Plate 17, 29′–i.
- *Peduncle.*—Length: Very long. Strength: Very heavy and strong. Color: Light Bice Green, Plate 17, 29′–i.
- *Opening.*—Bud opens well; does not ball.

Bloom:
- *Size.*—Very large; from 5½ inches to 6 inches when fully open.
- *Borne.*—Singly, but occasionally with one extra side bloom.
- *Stems.*—Long (from 18 inches to 26 inches); very strong.
- *Form.*—When first open: High-centered. When fully open: Outer petals partially quilled and inner petals mostly flat.
- *Petalage.*—From 50 to 60 petals.
- *Color.*—Both inside and outside of petals near white, lightly shaded with Seafoam Yellow, Plate 31, 25″–f, with base of petals shaded with Light Chelcedony Yellow, Plate 17, 25′–d on the inside; no discoloration after three days indoors.
- *Fragrance.*—Slight. Nature: Tea.

Petals:
- *Texture.*—Thick.
- *Surface.*—Satiny.
- *Form.*—Very broad; nearly round.
- *Persistance.*—Drop off cleanly after 4 or 5 days under room conditions.

REPRODUCTIVE ORGANS

Stamens: Medium length; arranged regularly around styles.

Anthers:
- *Color.*—Naples Yellow, Plate 16, 19′–d.

Filaments: Medium length.
- *Color.*—Nearly white.

Styles: Irregular length; thin; some petaloids mixed in.

PLANT

Form: Bush; upright; spreading.

Growth: Very vigorous.

Foliage: Compound of 5–7 leaflets.
- *Size.*—Very large.
- *Quantity.*—Abundant.
- *Color.*—New foliage: Bronzy. Old foliage: Upper side—Dusky Yellowish Green, Plate 41, 29‴–m. Lower side—Pois Green, Plate 41, 29‴–i.
- *Shape.*—Oval; bluntly pointed at apex.
- *Texture.*—Upper side: Leathery. Under side: Smooth, except for prickles on midrib.
- *Edge.*—Slightly serrated.

*Rachis.*—With numerous prickles on lower side. Color: Generally same color as leaves, lightly overcast with bronze; upper side of rachis at leaf axil is lighter green.

*Stipules.*—Relatively small; nearly smooth edge.

*Disease resistance.*—Very resistant to mildew and better than average resistance to blackspot, as determined by comparison with other rose varieties grown under the same conditions at Newark, N.Y.

Wood:

*New wood.*—Smooth surface. Color: Spanish Green, Plate 5, 29–m.

*Old wood.*—Smooth surface. Color: Forest Green: Plate 17, 29′–m.

Thorns:

*Quantity.*—On main stalks: Average. On laterals: Few.

*Form.*—Long base; pointing downward.

*Color (young).*—Dull Green Yellow, Plate 17, 27, shaded at base with Hazel, Plate 14, 11′–k.

Prickles: None.

What is claimed is:

1. A new and distinct variety of rose plant of the hybrid tea class, substantially as herein shown and described, characterized particularly as to novelty by the unique combination of a large plant size, exceptionally large and leathery leaves which are very resistant to mildew and blackspot, continuous flower production throughout the year when grown in the greenhouse, a classical, spiral opening flower form, with the flowers being borne on long and unusually thick stems, a distinctive and attractive white flower color, with the flowers being larger than those of any other white-flowered variety grown in the same environment, and very long keeping qualities of the flowers.

No references cited.

ROBERT E. BAGWILL, Primary Examiner